(12) United States Patent
McClellan et al.

(10) Patent No.: US 12,121,416 B2
(45) Date of Patent: Oct. 22, 2024

(54) STATICALLY CHARGED AND RECHARGEABLE SCAR MODULATION DRESSING

(71) Applicants: William T. McClellan, Morgantown, WV (US); Justin Chambers, Morgantown, WV (US)

(72) Inventors: William T. McClellan, Morgantown, WV (US); Justin Chambers, Morgantown, WV (US)

(*) Notice: Subject to any disclaimer, the term of this patent is extended or adjusted under 35 U.S.C. 154(b) by 557 days.

(21) Appl. No.: 17/440,734

(22) PCT Filed: Feb. 25, 2020

(86) PCT No.: PCT/US2020/019616
§ 371 (c)(1),
(2) Date: Sep. 17, 2021

(87) PCT Pub. No.: WO2020/176452
PCT Pub. Date: Sep. 3, 2020

(65) Prior Publication Data
US 2022/0211547 A1    Jul. 7, 2022

Related U.S. Application Data

(60) Provisional application No. 62/809,992, filed on Feb. 25, 2019.

(51) Int. Cl.
*A61F 13/00* (2024.01)
*A61N 1/20* (2006.01)
*A61N 1/26* (2006.01)

(52) U.S. Cl.
CPC ........ *A61F 13/00051* (2013.01); *A61N 1/205* (2013.01); *A61N 1/26* (2013.01); *A61F 2013/0028* (2013.01)

(58) Field of Classification Search
None
See application file for complete search history.

(56) References Cited

U.S. PATENT DOCUMENTS

| | | | |
|---|---|---|---|
| 4,142,521 | A | 3/1979 | Konikoff |
| 5,602,712 | A | 2/1997 | Daifuku et al. |
| 7,921,500 | B2 | 4/2011 | Linzell |
| 2002/0082668 | A1 | 6/2002 | Ingman |
| 2008/0033334 | A1 | 2/2008 | Gurtner et al. |

(Continued)

FOREIGN PATENT DOCUMENTS

JP     H03249777     11/1991

OTHER PUBLICATIONS

Lee et al., The Progress of PVDF as a Functional Material for Triboelectric Nanogenerators and Self-Powered Sensors, Micromachines 2018, 9, 532. (Year: 2018).*

(Continued)

*Primary Examiner* — Kim M Lewis
(74) *Attorney, Agent, or Firm* — Andrew D. Wright; Calderon Safran & Wright P.C.

(57) ABSTRACT

In a first aspect, there is a system including: a sheet configured to be applied to the skin of a patient over a wound or scar bed; a device that is separate from the sheet and that is configured to be used to massage the sheet to cause: (1) static charging of the sheet, and (2) physical massaging of the wound covered by the sheet.

23 Claims, 6 Drawing Sheets

(56) References Cited

U.S. PATENT DOCUMENTS

| | | | |
|---|---|---|---|
| 2008/0275374 A1* | 11/2008 | Smithers | A61N 1/40 602/41 |
| 2010/0056626 A1 | 3/2010 | Scuderi | |
| 2014/0345639 A1 | 11/2014 | Samain et al. | |
| 2017/0055601 A1 | 3/2017 | Ramirez | |
| 2019/0029886 A1 | 1/2019 | Lin | |

OTHER PUBLICATIONS

International Search Report and Written Opinion of the International Searching Authority from PCT Application No. PCT/US20/19616 dated Jul. 2, 2020, 10 pages.

Li-Tsang et al., "A prospective randomized clinical trial to investigate the effect of silicone gel sheeting (Cica-Care) on post-traumatic hypertrophic scar among the Chinese population", Jan. 10, 2006, 6 pages.

Shin et al., "The Role of Massage in Scar Management: A Literature Review", Mar. 2012, 10 pages.

* cited by examiner

STATICALLY CHARGED AND RECHARGEABLE SCAR MODULATION DRESSING

FIELD OF THE INVENTION

Aspects of the invention generally relate to medical devices and associated methods of manufacture and use, and more particularly to scar modulation dressings. Aspects of the invention relate to improving wound healing and improving scar maturation.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Various methods to improve wound healing and improve scar maturation include: Electro therapy (Electric fields, potentials and currents); reduced tension on the scar; scar massage; water retention and gas exchange; antibacterial interfaces (e.g. Nano-silver layer) and sunlight protection. Electro-therapy for the treatment of wounds and scar formation often requires large components/devices, batteries, etc., and are not practical for everyday wear. Scar tension reduction has shown benefits for improving scar maturation but is often obsolete with the proper internal suturing techniques.

Silicone sheeting may also be used for scar treatment and management. Silicone sheeting and its effects have been well documented but the working principles and mechanisms still up for debate. Many believe that silicone sheeting provides the optimal moisture retention and pressure characteristics for scar management. Others have thought that silicone's affinity for static electricity build up may play a role in scar management. More specifically by improving the body's natural response to wound closure (i.e., the skin battery effect).

Massage has also been shown to improve scar management and is often recommended by many surgeon's post-operation to reduce scarring.

Aspects of the invention generally relate to medical devices and associated methods of manufacture and use, and more particularly to scar modulation dressings. Aspects of the invention relate to improving wound healing and improving scar maturation.

Figure 1:
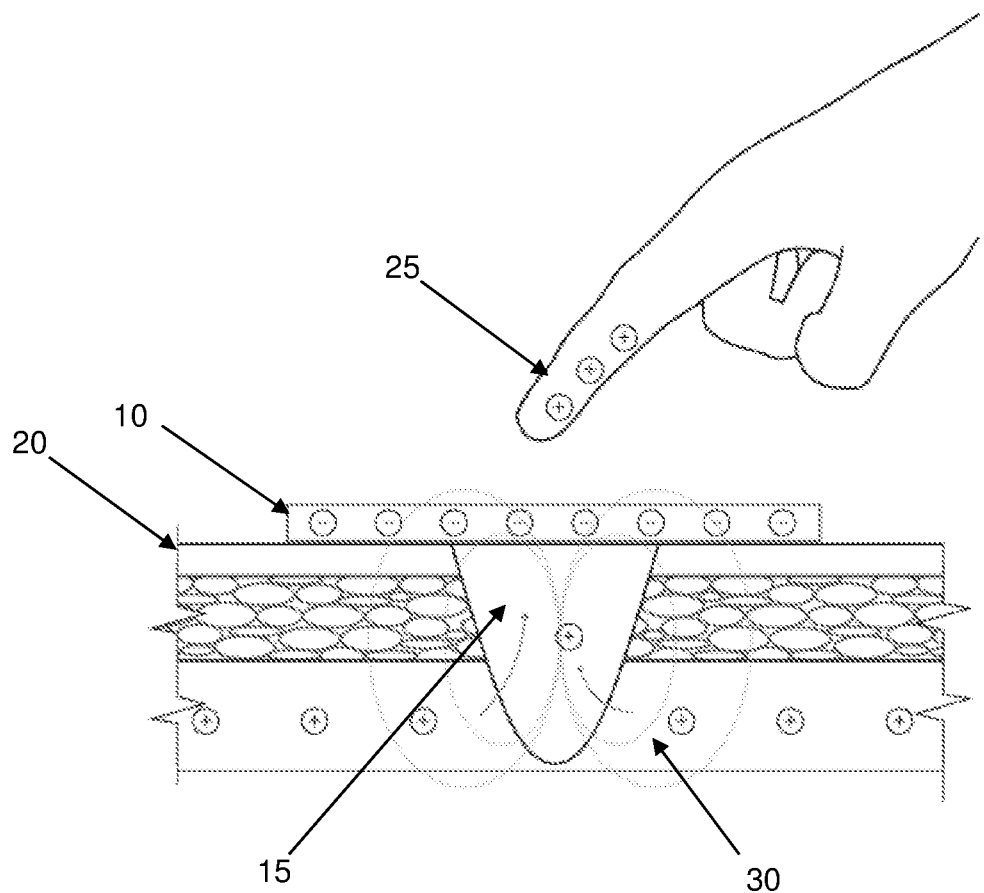
FIG. 1 shows a first system in accordance with aspects of the invention.

As shown in FIG. 1, a preferred embodiment involves applying a silicone sheet 10 (or a similar highly negative material on the triboelectric ("tribo") series, e.g., teflon, PVC, Polypropylene, etc.) to the wounded or scar area 15 at the patient's skin 20. A glove 25 (or other device) constructed out of a material that is highly positive on the tribo series (Such as Nylon, Wool, Silk or any other material on the positive side of the triboelectric series) is used to massage the wound or scar area.

This provides a dual benefit:

1) The contact of the glove/device 25 against the silicone sheeting 10 causes an electron exchange from the glove/device 25 to the silicone sheeting 10. Upon separation the silicone will result in a highly negative charge state while the glove/device will result in a highly positive charge state. Since silicone is an insulator, a static charge build-up will occur as a result of this contact and separation. This build-up of electrons on the surface of the silicone 10 makes the silicone sheeting 10 highly negative in charge. When the silicone sheeting 10 is in adhesive contact with the skin 20, which will act as a conductor due to its moisture and sodium content, the negatively charged silicone sheeting 10 will attract protons to move to the surface of the skin inducing a current 30. This current 30 is thought to align fibroblast and influence cell migration to the wounded area. This is especially true when the wound 15 has closed and the wound's natural electrical potential has diminished throughout the later stages of scar maturation.

2) The physical massage of rubbing the glove/device 25 against the silicone sheeting 10 helps to soften the scar tissue and improve blood flow, amongst other benefits.

Static charge is created on the silicone sheeting when two insulators come into contact. The two insulators each have a different affinity to either attract or easily lose electrons based on how they are ranked in the tribo series. When two insulators that are on different ends of the tribo series come into contact electrons will be transferred. When separated one material will come away highly negative and the other highly positive. The electrons will stay static on the surface until they are grounded or dissipated into the air via moisture vapor (i.e. humidity). This will neutralize the charge of the surface. Often high moisture content in the surrounding area will allow electrons to "leak" to the surroundings. This is why static electricity builds up well in dry environments.

In experiments, the inventors have observed that the silicone sheeting 10 tends to have a steady state charge of around −0.02 kv before tribocharging. After tribocharging in the manner described herein (e.g., by contacting the silicone sheeting 10 with the glove/device 25), the inventors have observed the silicone sheeting 10 to have an average charge of about −2.0 kv but as high as −8.0 kv. In extremely dry environments higher charges can be achieved. Humidity has a large role in charge capacity and charge duration. In low humidity conditions charge can last for days. In high humid conditions a charge may last as short as a few minutes.

Figure 2:
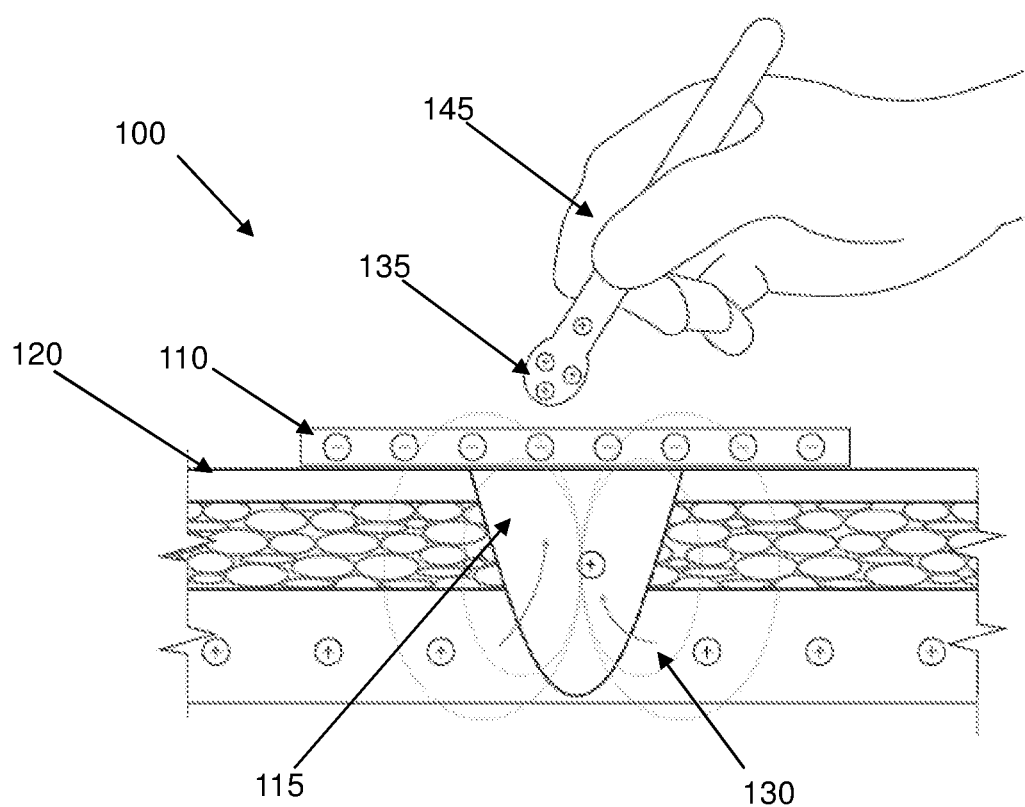
FIG. 2 shows a second system in accordance with aspects of the invention.

FIG. 2 shows an alternative embodiment to FIG. 1 in accordance with aspects of the invention. In particular, FIG. 2 shows a wound dressing system 100 comprising of a silicone sheet 110 (or a similar highly negative material on the triboelectric ("tribo") series, e.g., teflon, PVC, polypropylene, etc.) applied to the wounded or scar area 115 at the patient's skin 120. A device 135 (e.g., a stylus, wand, or other hand-held device), constructed out of a material that is highly positive on the tribo series (such as nylon, wool, silk or any other material on the positive side of the triboelectric series), held in the patients hand 145 and used to massage sheeting 110 on the wound or scar area 115. During such charging, the silicone bottom layer 110 collects free electrons from the device 135 to build a static charge on the surface of the silicone bottom layer 110. Surface modifications may be added to the materials to improve charge transfer efficiency. After tribocharging in the manner described herein, the charged silicone sheeting bottom layer 110 affects the skin 120 by creating a current 130 in a manner similar to that described with respect to FIG. 1, which results in improved healing for the wound 115. Also, similar to FIG. 1, the massaging of the dressing 100 has the dual effect of: (1) tribocharging the silicone bottom layer 110, and (2) physically massaging the wound 115.

Figure 3:
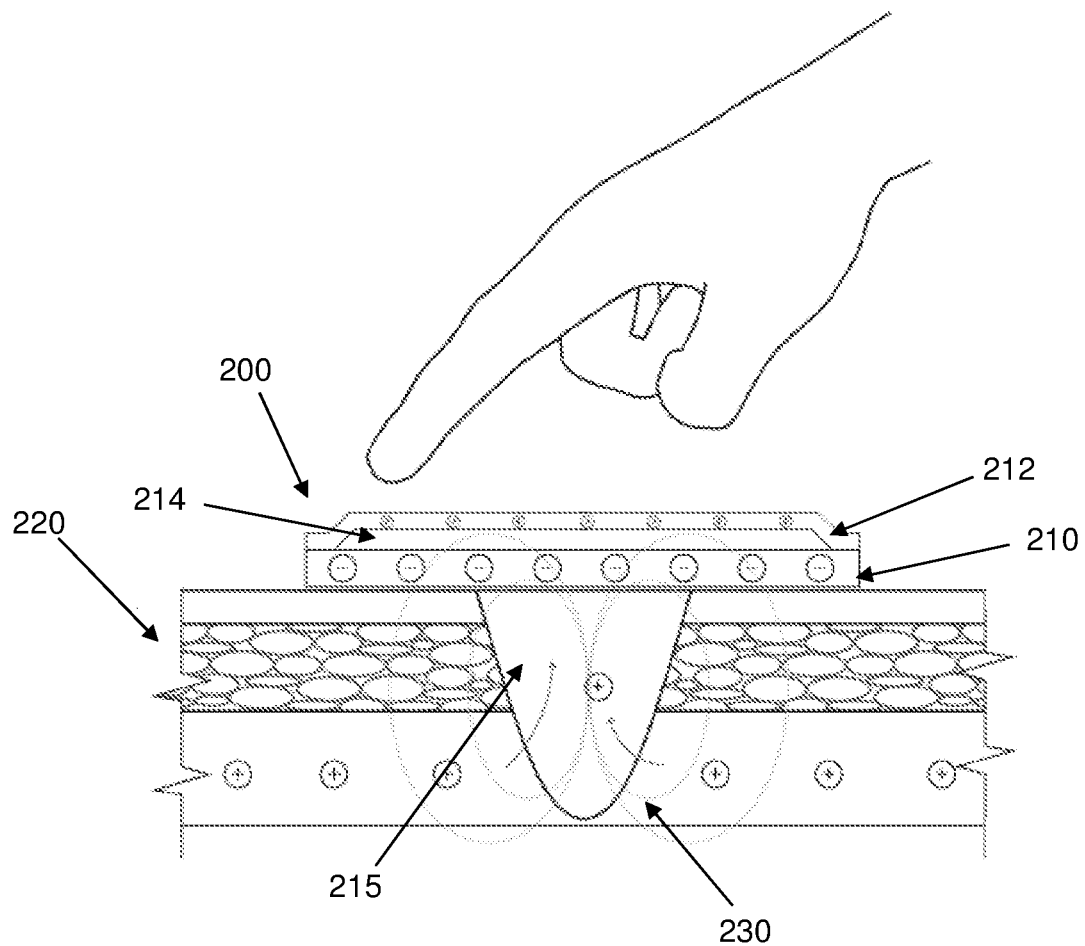
FIG. 3 shows a third system in accordance with aspects of the invention.

FIG. 3 shows an alternative embodiment in accordance with aspects of the invention. In particular, FIG. 3 shows a wound dressing 200 comprising a Multilayer Composite Sheeting that is configured to create a triboelectric nanogenerator (TENG). In embodiments, the wound dressing comprises: a material highly negative based on the triboelectric series (such as silicone, teflon, PVC, etc.), as the bottom layer 210 (similar to sheet 10) with an upper layer 212, comprised of a material highly positive on the triboelectric series (Such as nylon, wool, etc.), sealed around its edges and separated by a gas layer 214. In a preferred embodiment, the upper layer is nylon. This embodiment allows the patient to massage the dressing 200 which will cause the upper layer 212 to make variable contact and separation with the silicone bottom layer 210 allowing a charge transfer due to tribocharging. During such charging, the silicone bottom layer 210 collects free electrons from the upper layer 212 to build a static charge on the surface of the silicone bottom layer 210. The sealed gas layer 214 may be filled with nitrogen or other gases to reduce moisture content and charge equalization back to the upper layer 212. Surface modifications may be added to the materials to improve charge transfer efficiency and charge retention sealed pockets in a grid pattern may be made in a sheet to cut to size. After tribocharging in the manner described herein, the charged silicone bottom layer 210 affects the skin 220 by creating a current 230 in a manner similar to that described with respect to FIG. 1 and FIG. 2, which results in improved healing for the wound 215. Also, similar to FIG. 1 and FIG. 2, the massaging of the dressing 200 has the dual effect of: (1) tribocharging the silicone bottom layer 210, and (2) physically massaging the wound 215.

Figure 4:
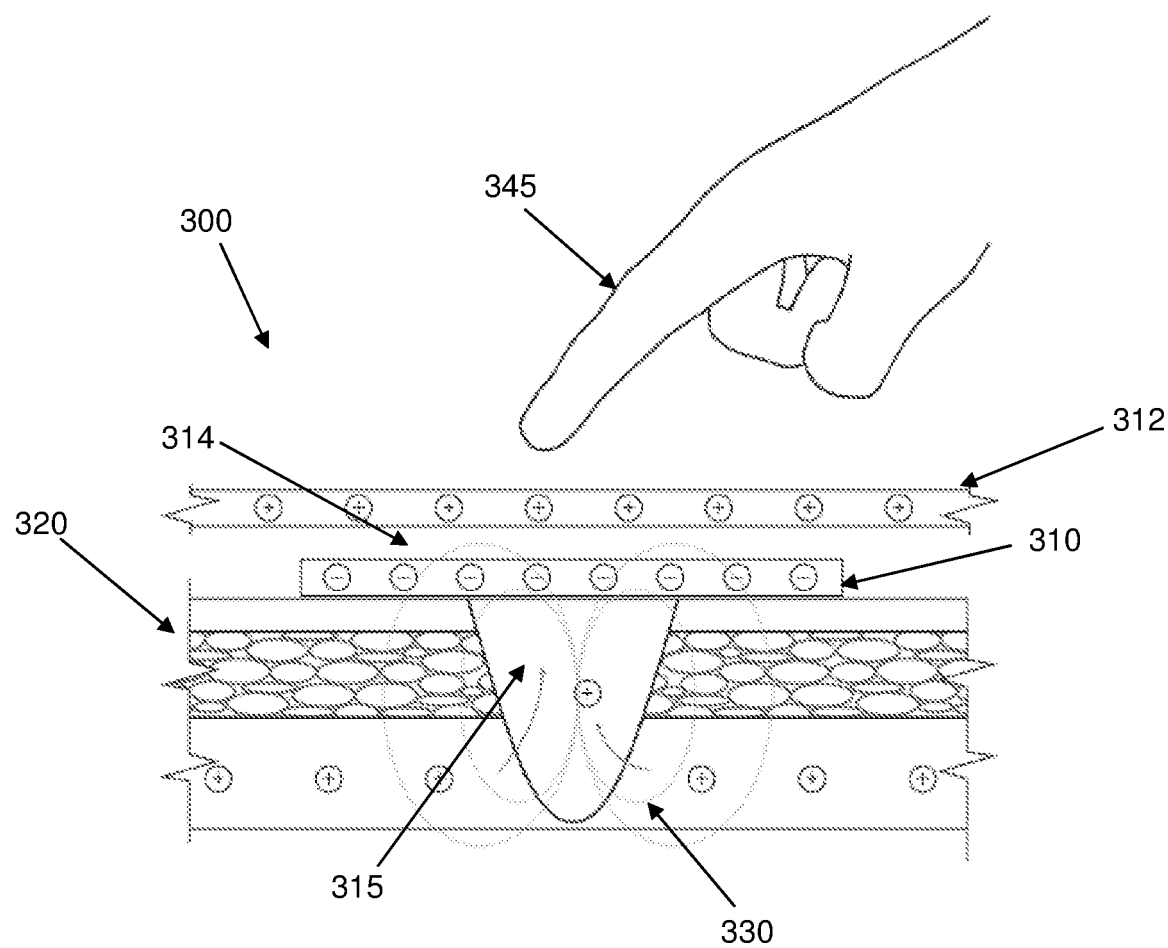
FIG. 4 shows a fourth system in accordance with aspects of the invention.

FIG. 4 shows an alternative embodiment in accordance with aspects of the invention. In particular, FIG. 4 shows a wound dressing 300 comprising of sheeting 310 covering the wound area 315. The sheeting 310 is then covered with an outer layer 312. This outer layer covering 312 can be part of a patients clothing. The combination of the outer layer covering 312 and sheeting 310 is configured to create a triboelectric nanogenerator (TENG) when the patient moves or when massaged. In a preferred embodiment, the sheeting 310 is a material highly negative based on the triboelectric series (such as silicone, teflon, PVC, etc.) and the outer layer 312 is a material that is highly positive on the tribo series (such as nylon, wool, silk or any other material on the positive side of the triboelectric series). Movement will cause the outer layer 312 to make variable contact with the sheeting 310. Massage with the patients hand 345 will also allow for variable contact with the sheeting. In embodiments, the wound dressing comprises: a silicone bottom layer 310 (similar to sheet 10) with an outer layer covering 312 and a separation 314 until motion of the patient or massage causes variable contact of the outer layer 312 with the sheeting 310. This embodiment allows the patient to massage the dressing 300 through the outer layer 312 which will cause the outer layer 312 to make variable contact with the silicone bottom layer 310 allowing a charge transfer due to tribocharging. During such charging, the silicone bottom layer 310 collects free electrons from the outer layer 312 to build a static charge on the surface of the silicone bottom layer 310. Surface modifications may be added to the materials to improve charge transfer efficiency. After tribocharging in the manner described herein, the charged silicone sheeting bottom layer 310 affects the skin 320 by creating a current 330 in a manner similar to that described with respect to FIG. 1, which results in improved healing for the wound 315. Also, similar to FIG. 1, the massaging of the dressing 300 has the dual effect of: (1) tribocharging the silicone bottom layer 310, and (2) physically massaging the wound 315.

Additional aspects of embodiments of the invention may include one or more of: surface modifications to the silicone or nylon sheeting; silicone additives; and modified massage glove/device designs. These modifications may be made to increase the efficiency or effectiveness of the wound dressing.

In embodiments, surface modifications to the materials include one or more of: increased surface roughness; nano-textures; increased surface area; and charge traps—surface area traps that can trap electrons. Any of these can be applied to any one or more of: the silicone sheeting 10; glove 25; the silicone bottom layer 110, 210, 310; the upper layer 212; the device 135; and the outer sheeting 312.

In embodiments, silicone additives include one or more of: thermochromic pigment to show temperature change; electrochromatic pigments to show charge state by changing colors; and UV inhibitor to block sunlight. Any of these can be applied to any one or more of: the silicone sheeting 10; the silicone bottom layer 110, 210, 310.

In embodiments, modified massage glove/device designs may include: nano-hair (e.g., Suede leather)—increases contact surface area. This may be applied to the glove/device 25.

Implementations as described herein provide an improvement in scar quality by providing a system that simultaneously provides a combination of both massage of the scar and the ability to have a more robust and rechargeable static electric charge. Massage with the glove/device/upper/outer layer serves two purposes. Direct massage directly improves the scar. Indirectly, it charges the silicone sheeting/bottom layer, which has a longer acting effect on the appearance of the scar. In embodiments, the material is slick to help with lowering friction and skin irritation during the massage.

In embodiments descried herein, the dressing may be composed of materials that are optimal for accepting a static charge and the slow release of that charge. The charge may or may not have a small magnetic field. The dressing may have an internal structure or components to control electron flow. The skin facing component may have filaments that touch or traverse the dressing. Alternatively, the charge may be created and stored using different materials that have same properties as filaments. Filaments within the dressing may go completely through the dressing and touch the skin and/or the wound.

In embodiments described herein, the dressing provides scar therapy including: direct pressure via massage; ideal moisture vapor transmission rate via pore system' and rechargeable static electric charged materials. Moisture vapor transmission rate (MVTR) of the dressing plays a role in the scar healing. Scar research has pointed to hydration of the wound as an important mechanism in causing fibroblasts and keratinocytes to synthesize and release collagen. MVTR is evident in the IV3000 dressing that the inventor has perfected for finger trauma. It is evident that too much moisture causes maceration of the skin which leads to infection and skin breakdown. Too much water loss leads to overactive cells. Therefore, ideal MVTR is important for scar development.

Figure 5:
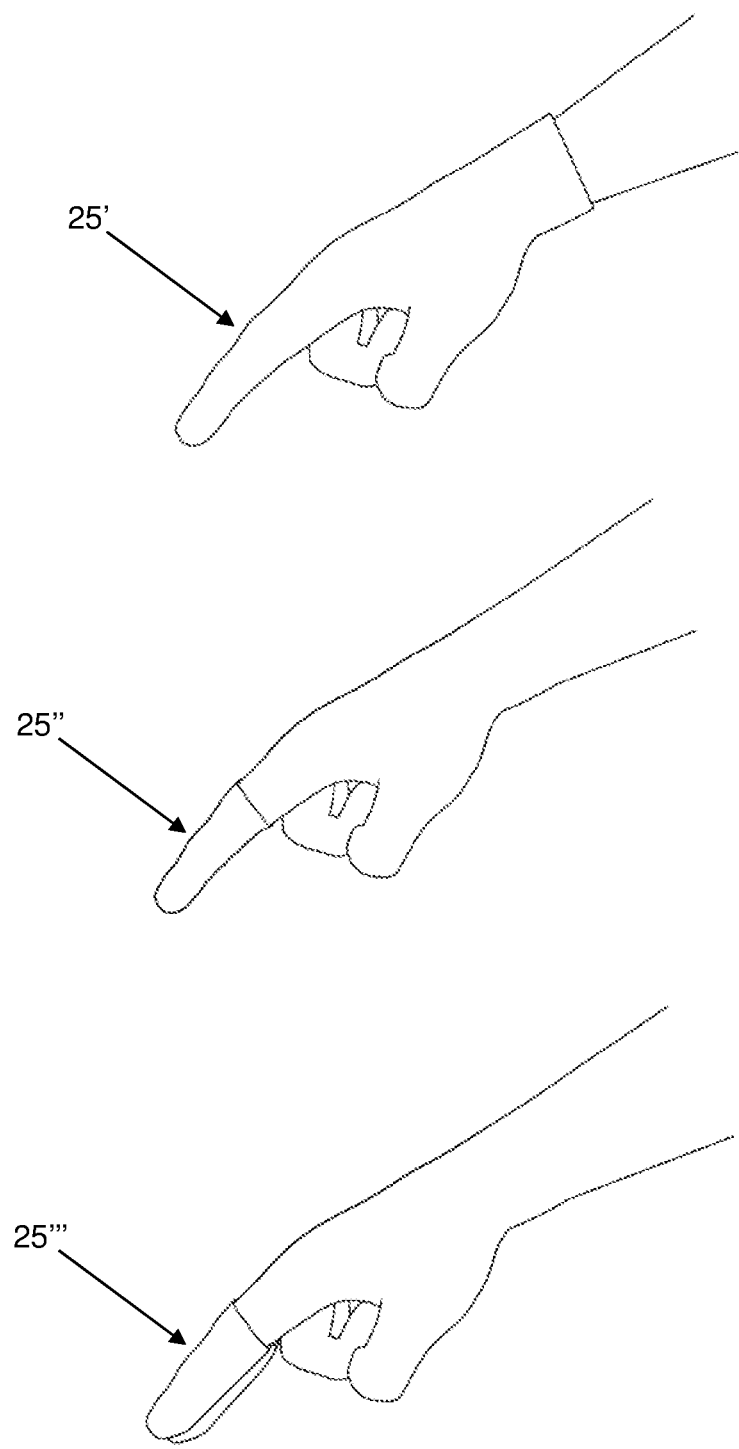
FIG. 5 shows additional details of the systems in accordance with aspects of the invention.

In an exemplary method of use of implementations of the invention, a statically charged dressing is placed over a wound. The dressing may comprise the sheeting 10, the bottom layer 110, the bottom layer 210, or the bottom layer 310. Pores may be arranged within the sheeting/bottom layer 10/110/210/310 and may be configured to optimize MVTR. As shown in the figures, a charging massage cloth or device is rubbed over the dressing sheeting/bottom layer 10/110/210/310 on the scar with some pressure, a few times per day. The charging massage cloth may be the glove 25, device 135, the upper layer 212, or the outer layer 312. FIG. 5 shows different embodiments of the glove 25. In one embodiment shown in FIG. 5, the glove 25' is a full hand glove that has four fingers and a thumb. In another embodiment shown in FIG. 5, the glove 25" is a one-finger glove that has only a single finger portion configured to receive one finger of a user. In another embodiment shown in FIG. 5, the glove 25'" is a two-finger glove that has only two finger portions configured to receive two fingers of a user. Its composition helps to create a negative or positive charge into the dressing. As described herein, a static charged field is created in the dressing, and the composition of the dressing holds and discharges the charge into the skin around the wound in a controlled fashion.

Embodiments may include a capacitor-like dressing that includes porous holes to balance the moisture vapor transmission rate (MVTR). The capacitor-like dressing may represent any of the sheeting/bottom layer 10/110/210/310 and may have metallic or fiber inserts within the dressing to create, hold, or systematically discharge the charge. In some embodiments, the dressing may include an adhesive along the layer that touches the skin. In embodiments, the adhesive is applied only around a perimeter of the layer that contacts the skin, e.g., sheeting/bottom layer 10/110/210/310. In this manner, the layer is adhered to the skin by the adhesive, while a central part of the layer directly contacts the skin and/or wound (i.e., without any adhesive at the location(s) of direct contact).

In embodiments the glove 25, device 135, upper layer 212, or outer layer 312 comprises a low-friction charging cloth/material to be rubbed onto the dressing material to elicit a charge in the dressing. This material will serve as a mechanical massage aid.

In embodiments the materials should be soft, pliable, and may contain pores to create ideal moisture vapor transmission rate. The dressing may be configured to change color with the amount of charge left. For example, green when it has charge and is active, and red when it is without charge.

In embodiments, the sheeting/bottom layer 10/110/210/310 includes a channel or divot on the side that touches the skin, the channel or divot being filled with scar cream.

Additional aspects of the invention include manufacturing a system comprising the sheeting/bottom layer 10/110/210/310 and the glove 25, device 135, upper layer 212, or outer layer 312 as described herein. Further aspects of the invention include a method of using the system comprising the sheeting/bottom layer 10/110/210/310 and the glove 25, device 135, upper layer 212, or outer layer 312 as described herein. Even further aspects of the invention include providing instructions for using the system comprising the sheeting/bottom layer 10/110/210/310 and the glove 25, device 135, upper layer 212, or outer layer 312 described herein. The instructions may be at least one of printed and video.

Additional aspects of the invention include manufacturing a dressing as described herein. Further aspects of the invention include a method of using the dressing as described herein. Even further aspects of the invention include providing instructions for using the dressing described herein. The instructions may be at least one of printed and video.

Figure 6:
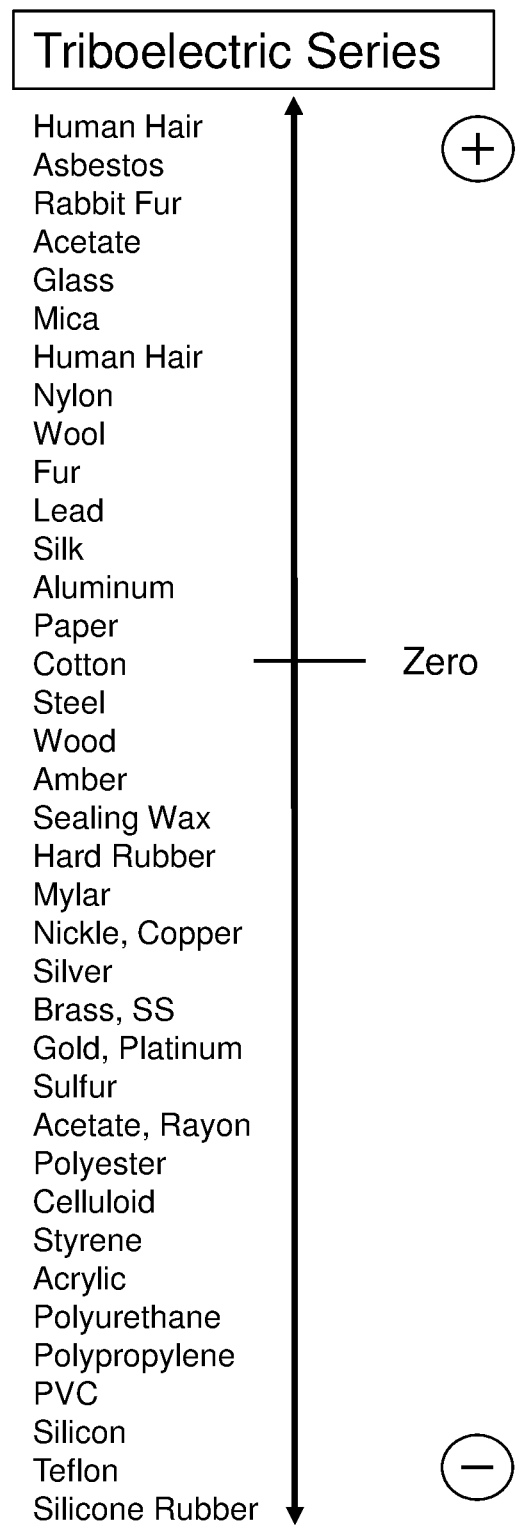
FIG. 6 shows examples of some materials on the tribo series.

FIG. 6 shows examples of some materials on the tribo series. As used herein, a material that is highly negative on the tribo series is a material that is on the negative side of the series and that is closer to the negative end of the scale (e.g., silicone rubber) than to zero (e.g., cotton/steel), and material that is highly positive on the tribo series is a material that is on the positive side of the series and that is closer to the positive end of the scale (e.g., human hands) than to zero (e.g., cotton/steel).

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A system, comprising:
a sheet configured to be applied to skin of a patient over a wound or scar bed;
a device that is separate from the sheet and that is configured to be used to massage the sheet to cause: (1) static charging of the sheet, and (2) physical massaging of the wound covered by the sheet,
wherein the device is a glove that fits on a finger, multiple fingers or a hand of a user.

2. The system of claim 1, wherein:
the sheet is composed of a material that is highly negative on the triboelectric series; and
the device is composed of a material that is highly positive on the triboelectric series relative to the sheet.

3. The system of claim 2, wherein:
the sheet is composed of silicone; and
the device is composed of nylon.

4. The system of claim 2, wherein the sheet comprises pores that affect a moisture vapor transmission rate of the system.

5. The system of claim 2, wherein the sheet comprises an adhesive on a side that contacts the skin.

6. The system of claim 2, wherein the sheet comprises at least one of: manufactured surface roughness; nano-textures; increased surface area; and charge traps.

7. A method comprising manufacturing the system of claim 1.

8. A method of using the system of claim 1, the method comprising:
applying the sheet to the skin over the wound; and
massaging the sheet with the device plural times each day for a predefined number of days.

9. A system, comprising:
a sheet configured to be applied to skin of a patient over a wound or scar bed;
an upper layer connected to the sheet; and
a layer of gas sealed between the sheet and the upper layer,
wherein the upper layer is configured to be used to massage the sheet to cause: (1) static charging of the sheet, and (2) physical massaging of the wound covered by the sheet.

10. The system of claim 9, wherein:
the sheet is composed of a material that is highly negative on the triboelectric series; and
the upper layer is composed of a material that is highly positive on the triboelectric series relative to the sheet.

11. The system of claim 10, wherein:
the sheet is composed of silicone; and
the upper layer is composed of nylon.

12. The system of claim 10, wherein the sheet comprises pores that affect a moisture vapor transmission rate of the system.

13. The system of claim 10, wherein the sheet comprises an adhesive on a side that contacts the skin.

14. The system of claim 10, wherein the sheet comprises at least one of: manufactured surface roughness; nano-textures; increased surface area; and charge traps.

15. A method comprising manufacturing the system of claim 9.

16. A method of using the system of claim 9, the method comprising:
applying the sheet to the skin over the wound; and
massaging the sheet via the upper layer plural times each day for a predefined number of days.

17. A system, comprising:
a sheet configured to be applied to skin of a patient over a wound or scar bed;
an upper layer configured to cover at least part of the sheet; and
an area of separation between the sheet and the upper layer,
wherein the upper layer is configured to make variable contact with the sheet during a patient's movement to create a static charge on the sheet.

18. The system of claim 17, wherein:
the sheet is composed of a material that is highly negative on the triboelectric series; and
the upper layer is composed of a material that is highly positive on the triboelectric series relative to the sheet.

19. The system of claim 18, wherein:
the sheet is composed of silicone; and
the upper layer is composed of nylon.

20. The system of claim 18, wherein the sheet comprises an adhesive on a side that contacts the skin.

21. The system of claim 18, wherein the sheet comprises at least one of: manufactured surface roughness; nano-textures; increased surface area; and charge traps.

22. A method comprising manufacturing the system of claim 17.

23. A method of using the system of claim 17, the method comprising:
applying the sheet to the skin over the wound; and
massaging the sheet with the upper layer plural times each day for a predefined number of days.

* * * * *